Feb. 18, 1964 R. S. MOORE Plant Pat. 2,366
MINIATURE ROSE PLANT
Filed Sept. 13, 1962
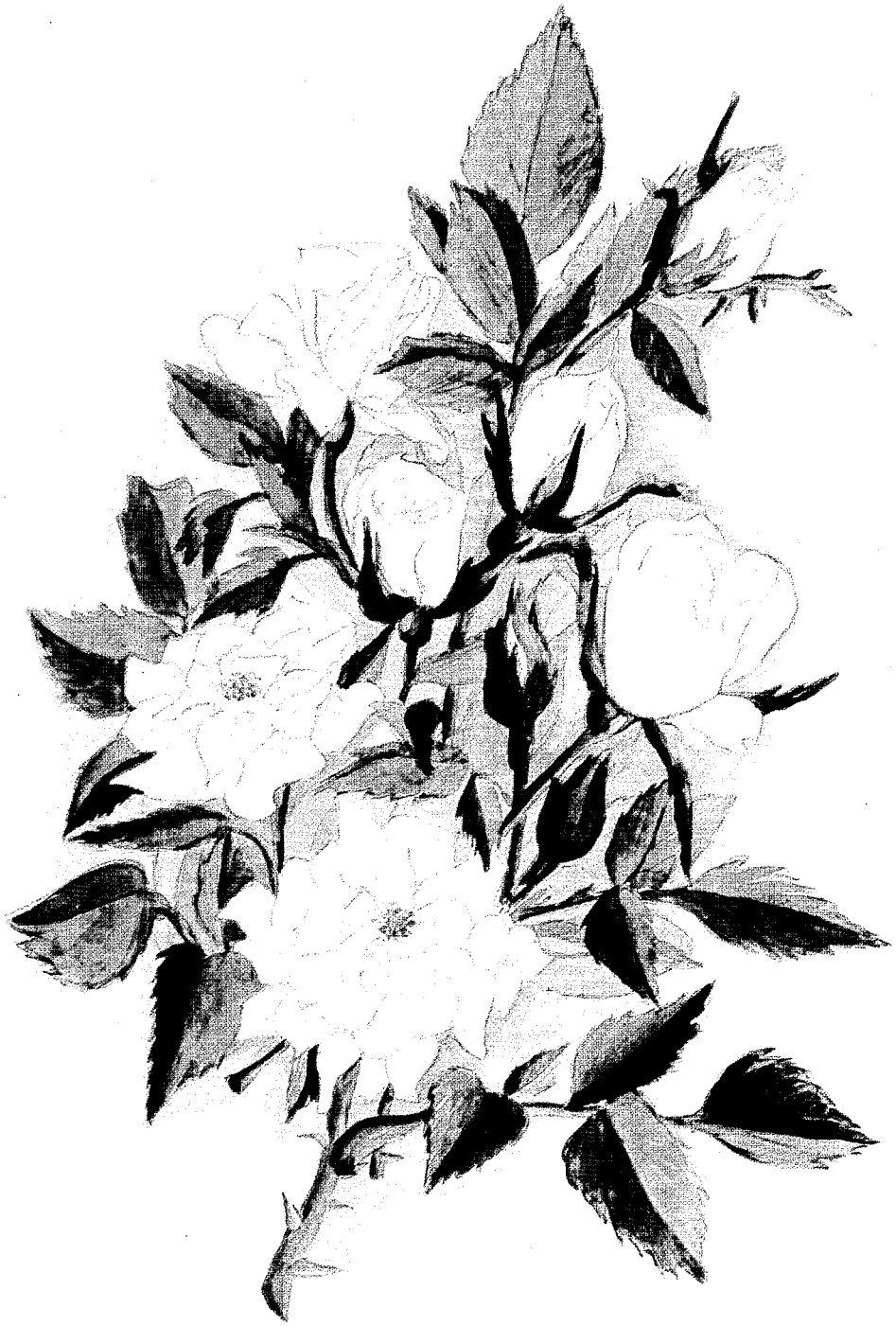
WITNESS
Jeanette Nunn Copley
INVENTOR
Ralph S. Moore
ATTORNEYS
Webster & Webster United States Patent Office Plant Pat. 2,366
Patented Feb. 18, 1964

2,366
MINIATURE ROSE PLANT

Ralph S. Moore, 2519 E. Mineral King, Visalia, Calif.

Filed Sept. 13, 1962, Ser. No. 223,567
1 Claim. (Cl. Plt.—8)

This invention is directed to a new and distinct variety of hardy, dwarf, bush type rose plant of the hybrid miniature class.

The variety is of the same parentage as the white flowering Easter Morning (United States Plant Patent No. 2,177), and of general similarity in plant, growth, and bloom, including buds and mature flowers. Also, the flowers are similar to Frosty (United States Plant Patent No. 1,412).

The present variety of miniature rose plant, which blooms from spring to frost, is distintively characterized, as to novelty, by:

Flowers whose petals are of softer texture, and often narrower, than those of Easter Morning.

A plant and flowers which are slightly larger than the average miniature, but which plant can be maintained low and neat by pruning.

A good, much branched, early and abundantly flowering plant which can be propagated from cuttings and grown to marketable size faster and easier than any other of the white flowering miniature roses, including Easter Morning; the variety thus being most satisfactory for economical mass production.

A plant which is especially adaptable for growing as a low hedge or garden border.

The variety was originated by me in my nursery located at Visalia, California, under conditions of careful control and observation, as a cross between Golden Glow (United States Plant Patent No. 263) as the seed parent, and Zee (unpatented) as the pollen parent; Zee being a miniature rose variety heretofore originated by me, used only for rose plant breeding, and which has not been introduced to the trade.

Subsequent to origination of the variety I successfully asexually reproduced it, in my nursery located as aforesaid, by budding as well as cuttings; the reproductions having run true in all respects.

The figure of the drawings illustrates a spray, including foliage, buds and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy; dwarf; bush; seedling; outdoor; greenhouse; garden decoration; cut flowers.
Class: Hybrid miniature.

*Flowers*

Continuity: Intermittent, continuous.
Flowers borne: Singly, several to stem, in irregular pyramidal cluster on normal medium length stems.
Quantity of bloom: Abundant, both outdoors and in greenhouse.
Bud:
*Peduncle.*—Long; slender, medium; erect; medium green; red hairs.
*Before calyx breaks.*—Size—small. Form—pointed, oval; with foliaceous parts extending beyond the tip of the bud equal to one-half of its length. Color—medium to light green.
*As calyx breaks.*—Color—creamy white to Dresden yellow, 64/3.
*As first petal opens.*—Size—small. Form—pointed, ovoid. Color—both outside and inside—white (sometimes pale yellow or cream). Opening—opens well in all weather.

Bloom:
*Size when fully open.*—Small, averaging 1½" to 1¾".
*Petalage.*—Double to very double, with from 35 to 50 petals arranged regularly.
*Form.*—Cupped, full, high center at first; becoming cupped. Petals remaining at first loosely rolled outward; becoming later at maturity loosely flat cupped.
Petals: Thin; leathery; satiny, both inside and outside.
*Shape.*—Outside—ovate, with apex nearly flat with small point in center. Intermediate—lanceolate. Inside—lanceolate.
*Color.*—Newly opened flower from plant grown outdoors (May 1962)—Outside petal: outside surface—white, base shaded soft uranium green, 63/3; inside surface—white, base shaded soft uranium green, 63/3. Intermediate petal: outside surface—white, base shaded soft uranium green, 63/2 to 63/3; inside surface—white, base shaded soft uranium green, 63/3, to Dresden yellow, 64/3. Inner petal: outside surface—near white, shading through soft yellow into Dresden yellow, 64/2, at base; inside surface—near white, shading through soft yellow into Dresden yellow, 64/2, at base. A flower that was open for three days outdoors (May 1962): All petals, both outside and inside surface, white—base tipped soft Dresden yellow, 64/3.
*General color effect.*—Newly opened flower—cream or cream white. Three days open—white.
*Behavior.*—Drops off cleanly.
*Flower longevity.*—Bush in garden—three to four days. Cut flowers kept at living room temperature—two to three days.

*Reproductive Organs*

Stamens: Few; arranged irregularly, partly about pistils; mixed with petaloids.
Filaments: Short, medium; yellow; few; most with anthers.
Anthers: Small, medium; yellow; open at various times.
Pollen: Sparse; lemon.
Pistils: Few, medium.
Styles: Even; short, medium; thin; bunched.
Stigma: Pale greenish yellow.
Ovaries: All enclosed in calyx.
Hips: Ovoid; reddish brown; moderately smooth; walls thin.
Sepals: Permanent; long; straight; spear shaped; fold back against stem; light green, becoming brownish.
Seeds: Very few; small.

*Plant*

Foliage:
*Leaves.*—Compound of 5 to 7 leaflets; normal abundance; moderately small; moderately thin; somewhat glossy.
*Leaflets.* — Shape — oval. Apex—acute. Base—round. Margin—serrate.
*Color.*—Mature—upper surface—normal green; under surface—light, normal green. Young—upper surface—normal green, overlaid or tinted bronze; under surface—light, normal green, overlaid or tinted bronze.
*Rachis.*—Medium. Upper Side—almost smooth. Under Side—sparsely prickly.
*Stipules.*—Long; narrow; with short points turning out at an angle of 45 degrees or more.

Growth:

*Habit.*—Dwarf; bushy; spreading.

*Growth.*—Vigorous.

*Canes.*—Medium.

*Main stems.*—Color—green, sometimes older stems gray-green. Thorns—several; short; straight or hooked slightly downward; short rounded base. Prickles—none, few. Hairs—none, few.

*Branches.*—Color—bright green. Thorns—several; short; hooked downward; short rounded base. Prickles—none. Hairs—none.

*New shoots.* — Color — green, tinted bronze. Thorns—few, several; short; straight; short round-base. Prickles—none. Hairs—none.

The miniature rose plant and its flowers as herein described may vary in slight detail due to climatic and soil conditions under which the variety may be grown; the present description being of the variety as grown at Visalia, California.

The following is claimed:

A new and distinct variety of much branched, spreading, early and abundantly white flowering, miniature rose plant of hardy, dwarf, bush type, as illustrated and described, characterized by a plant and flowers slightly larger than the average miniature rose, a plant which grows from cuttings to maturity faster and easier than any other of the white flowering miniature roses including Easter Morning, and a plant which blooms from spring to frost; and further characterized—in comparison with Easter Morning—by general resemblance in plant, growth, and bloom but distinctive in that the petals of the white flowers are of softer texture and often narrower.

No references cited.